United States Patent [19]

Zohler

[11] Patent Number: 4,724,591
[45] Date of Patent: Feb. 16, 1988

[54] METHOD FOR MEASURING THE PORE SIZE OF ENHANCED TUBES

[75] Inventor: Steven R. Zohler, Manlius, N.Y.

[73] Assignee: Carrier Corporation, Syracuse, N.Y.

[21] Appl. No.: 16,967

[22] Filed: Feb. 24, 1987

Related U.S. Application Data

[63] Continuation of Ser. No. 803,377, Dec. 2, 1985, abandoned.

[51] Int. Cl.$^4$ ............................................. B23Q 17/00
[52] U.S. Cl. .................................. 29/157.3 R; 29/407
[58] Field of Search .......................... 29/407, 157.3 R; 72/37.5, 49.1, 49.5, 49.8; 73/37 T, 37.5, 49.1, 49.5, 49.8

[56] References Cited

U.S. PATENT DOCUMENTS 3,863,492  2/1975  Trask, II .............................. 73/37.5

OTHER PUBLICATIONS

John and Haberman, *Introduction to Fluid Mechanics*, 2nd ed., Prentice Hall, Englwood Cliffs, NJ, 1971, p. 82.
Holman, *Heat Transfer*, 4th ed., McGraw Hill, New York, New York, 1976, p. 369.

*Primary Examiner*—Howard N. Goldberg
*Assistant Examiner*—Irene Graves Golabi
*Attorney, Agent, or Firm*—Robert H. Kelly

[57] ABSTRACT

A method of determining the average size of a plurality of pores on the external surface of an enhanced tube having subsurface channels connecting adjacent pores. A pressure measurement apparatus is positioned on a portion of the enhanced tube surface and regulated air supply pressure is blown into the pressure measurement apparatus whereby a portion of the air pressure escapes through the pores and subsurface channels. Accordingly, the difference between the supply pressure and the pressure lost across the pores and subsurface channels is a measurement of the pore size which correlates to the boiling heat transfer coefficient of the tube.

4 Claims, 6 Drawing Figures

METHOD FOR MEASURING THE PORE SIZE OF ENHANCED TUBES

This application is a continuation of application Ser. No. 803,377, filed Dec. 2, 1985, now abandoned.

BACKGROUND OF THE INVENTION

This invention relates generally to the manufacture of enhanced tubes and more particularly to a method for measuring the pore size in an externally enhanced evaporator tube.

In an evaporator of certain refrigeration systems a fluid to be cooled is passed through heat transfer tubing while refrigerant in contact with the exterior of the tubing changes state from a liquid to a vapor by absorbing heat from the fluid within the tubing. The external and internal configuration of the tubing is important in determining the overall heat transfer characteristics of the tubing. For example, it is known that one of the most effective ways of transferring heat from the fluid within the tube to the boiling refrigerant surrounding the tube is through the mechanism of nucleate boiling.

It is theorized that the provision of vapor entrapment sites or cavities cause nucleate boiling. According to this theory the trapped vapor forms the nucleus of a bubble, at or slightly above the saturation temperature, and the bubble increases in volume as heat is added until surface tension is overcome and a vapor bubble breaks free from the heat transfer surface. As the vapor bubble leaves the heat transfer surface, liquid refrigerant enters the vacated volume trapping the remaining vapor and another vapor bubble is formed. The continual bubble formation together with the convection effect of the bubbles traveling through and mixing the boundary layer of superheated liquid refrigerant, which covers the vapor entrapment sites, results in improved transfer. U.S. Pat. No. 3,301,314 discloses a heat exchange surface having a number of discrete artificial nucleation sites.

It is further known that a vapor entrapment site produces stable bubble columns when it is of the re-entrant type. In this context, a re-entrant vapor entrapment site is defined as a cavity or groove in which the size of the surface pore or gap is smaller than the subsurface cavity or subsurface groove. U.S. Pat. Nos. 3,696,861 and 3,768,290 disclose heat transfer tubes having such re-entrant type grooves.

Also, it is known that an excessive influx of liquid from the surroundings can flood or deactivate a vapor entrapment site. In this regard, a heat transfer surface having subsurface channels communicating with the surroundings through surface openings or pores having a specified "opening ratio" may provide good heat transfer and prevent flooding of the vapor entrapment site or subsurface channel.

In regard to the interior surface configuration of a heat transfer tube it is known that providing an internal rib on the tube may enhance the heat transfer characteristics of the tube due to the increased turbulence of the fluid flowing through the ribbed tube.

As disclosed in U.S. Pat. Nos. 4,425,696 and 4,438,807 assigned to the present assignee, and incorporated by reference herein, an internally and externally enhanced heat transfer tube, having an internal rib and an external groove—commonly referred to as a subsurface channel—communicating with the surrounding liquid through surface openings, i.e. pores, may be manufactured by a single pass process with a tube finning machine. According to the disclosed process a grooved mandrel is placed inside an unformed tube and a tool arbor having a tool gang thereon is rolled over the external surface of the tube. The unformed tube is pressed against the mandrel to form at least one internal rib on the internal surface of the tube. Simultaneously, at least one external fin convolution is formed on the external surface of the tube by the tool arbor with the tool gang. The external fin convolutions form subsurface channels therebetween. The external fin convolution has depressed sections above the internal rib where the tube is forced into the grooves of the mandrel to form the rib. A smooth roller-like disc on the tool arbor is rolled over the external surface of the tube after the external fin is formed. The smooth roller-like disc is designed to bend over the tip portion of the external fin to touch the adjacent fin convolution to form enclosed subsurface channels only at those sections of the external fin which are not located above the internal rib. The tip portion of the depressed sections of the external fin, which are located above an internal rib, are bent over but do not touch the adjacent convolutions thereby leaving pores which provide fluid communication between the fluid surrounding the tube and the subsurface channels.

The performance of the foregoing tube is critically dependent on the size of the subsurface channels and pores on the surface of the tube, and this performance may be enhanced by the internal ribs. It is therefore important to maintain a consistent subsurface channel size and pore size during the manufacturing process. Normal variations in subsurface channel size and surface pore size do occur, however, due to tool wear, dimensional and material variations in the tube lengths, and machine tolerances. In order to account for these variables and to maintain a consistent pore size, it is necessary to measure the pore size on each tube produced and adjust the finning machine to maintain the correct subsurface channel and pore sizes. However, the prior methods of having an operator randomly selecting manufactured tubes and optically checking the pore size of the selected tube under a microscope or using an image analyzer to compare the area of a pore in a photograph of a tube with the known area of a reference photograph were time consuming and did not provide the quality and quantity of tubes necessary for a manufacturing process. Not only were these very laborious and expensive practices, but they also cannot be used to check each and every tube in a manufacturing process.

Thus, there is a clear need for a method for measuring the size of the surface pores in an enhanced tube that will, to a large extent, overcome the inadequacies that have characterized the prior art.

SUMMARY OF THE INVENTION

A method of measuring the pore size in an enhanced tube in accordance with the principles of the present invention is characterized by producing an enhanced tube having a plurality of subsurface channels connected by pores spaced along the channels. Then, sealingly engaging a portion of the enhanced tube with a measuring device having a chamber in contact with the enhanced tube surface, whereby compressed air is blown into the pores on the surface of the enhanced tube and out the subsurface channels resulting in a pressure drop across the pores, thus giving a measurement of the average size of the pores on the enhanced tube. The air pressure drop across the pores on the tube correlates to the area of the pores on the tube, and thus relates to the expected boiling heat transfer coefficient of the tube.

Accordingly, it is an object of the present invention to provide a method which measures average pore size on an enhanced tube surface.

Another object of the present invention is to provide a method which can inspect 100% of the enhanced tubes that are produced.

A further object of the present invention is to provide a method which measures the average pore size on each tube produced and allows adjustment of the finning machine to maintain the correct pore size.

These and other objects of the present invention are attained by a method of measuring the pore size of an enhanced evaporator tube by blowing compressed air through the pores on the surface of the enhanced tube and recording the resulting pressure drop. According to the present invention, the resulting pressure drop is a measure of the average size of the pores on the tube. Also, correlations can be established which relate the air pressure drop across the pores on the tube to the expected boiling heat transfer coefficient of the tube.

Thus, the present invention provides a method of measuring the average pore size of an enhanced tube immediately after production and adjusting the finning machine for the manufacture of the next tube if the measured pore size is different than the desired pore size.

The various features of novelty which characterize the invention are pointed out with particularity in the claims annexed to and forming a part of this specification. For a better understanding of the invention, its operating advantages and specific objects attained by its use, reference should be had to the accompanying drawings and descriptive matter in which there is illustrated and described a preferred embodiment of the invention.

BRIEF DESCRIPTION OF THE DRAWINGS

Other objects and advantages of the present invention will be apparent from the following detailed description in conjunction with the accompanying drawings, forming a part of this specification, and in which reference numerals shown in the drawings designate like or corresponding parts throughout the same, and in which.

DESCRIPTION OF THE PREFERRED EMBODIMENT

The embodiment of the present invention described below is especially designed for use with enhanced evaporator tubes because these tubes have a critical dimension which must be precisely controlled to maintain good heat transfer performance. These enhanced tubes are designed for use in an evaporator of a refrigeration system having a fluid to be cooled passing through heat transfer tubes and having refrigerant, which is vaporized, in contact with the external surfaces of the tubes. Typically, a plurality of heat transfer tubes are mounted in parallel and connected so that several tubes form a fluid flow circuit and a plurality of such parallel circuits are provided to form a tube bundle. Usually, all of the tubes of the various circuits are contained within a single shell wherein they are immersed in the refrigerant. The heat transfer capabilities of the evaporator is largely determined by the average heat transfer characteristics of the individual heat transfer tubes. The size of the subsurface channels and pores on the surface of the tubes are particularly critical for R-11 applications. Therefore, it is important to maintain a consistent pore size during the manufacturing process of enhanced evaporator tubes.

Figure 1:
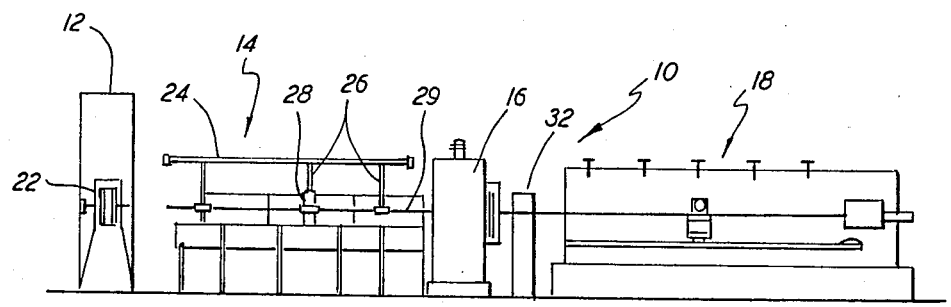
FIG. 1 is a schematic view of a finning machine for the manufacture of enhanced tubes in accordance with the present invention.
Figure 3:
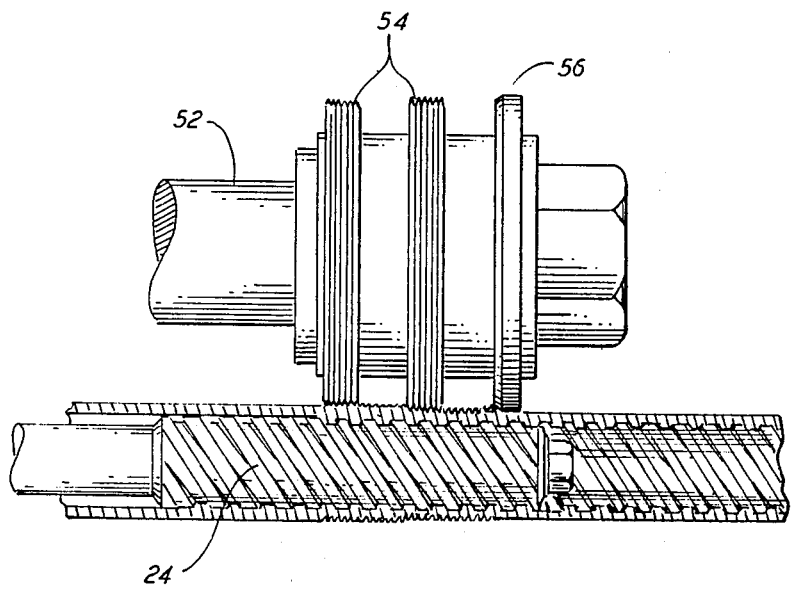
FIG. 3 is a side elevation view of one tool arbor of the finning head shown in FIG. 2 with a fragmentary sectional view of a tube on a mandrel.
Figure 2:
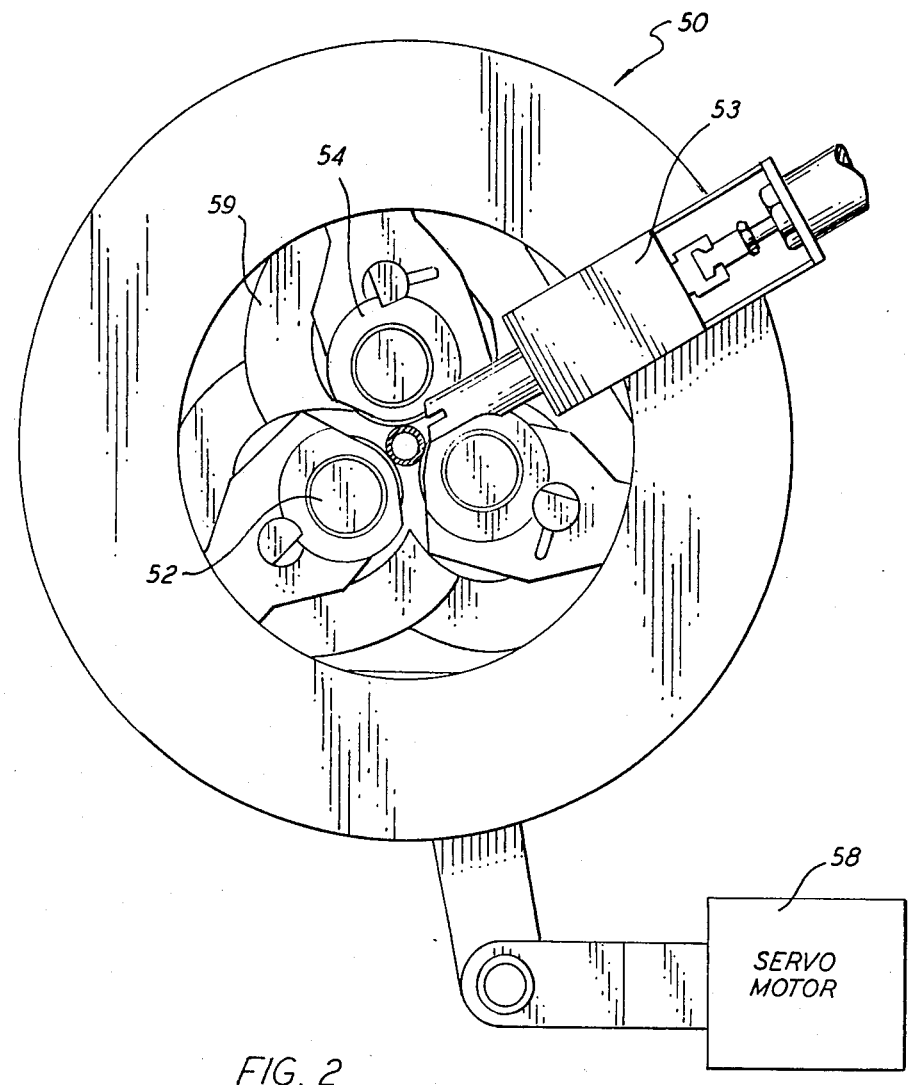
FIG. 2 is an enlarged elevation view of the finning head of the finning machine shown in FIG. 1.

Referring now to the drawings, FIG. 1 is a diagrammatic representation of a finning station for manufacturing enhanced tubes in accordance with the principles of the present invention. The finning station 10 includes an electronic control cabinet 12, a feed section 14, a finning head section 16, an ejection section 32 and a pore measurement section 18. The electronic control cabinet includes a programmable controller and an operator console 22 which perform logic execution, timing, sequencing, and calculations for the finning operation. The feed section 14 generally includes two similar parallel mandrels 24 (the two mandrels are generally in the same horizontal plane, and accordingly the rearward mandrel is not shown in the Figure) typically supported by a plurality of support arms 26 and positioned by piston means 28. Accordingly, the operator will load a blank tube on the front and rear mandrels 24 and cycle the feed section 14 such that one mandrel, e.g. the front mandrel, will drop down and move the blank tube along the longitudinal finning axis 29 into the finning head section 16. The finning head section 16, as shown in FIGS. 2 and 3, includes a finning head 50 having a plurality of tool arbors 52 and a tube locating device 53, which accurately positions the end of the blank tube within finning head 50 prior to the start of the finning process. Each of the tool arbors 52 includes a tool gang arrangement having a plurality of finning discs 54 and rollers 56 cooperating with the mandrel 24 to produce the enhanced tube. The finning discs 54, which are skewed at an angle to the longitudinal finning axis 29, inherently move the enhanced tube through the finning head section 16 to the ejection section 32. When the blank tube is completely enhanced the finning head 50 of the finning head section 16 will open, i.e. the tool arbors 52 will move radially outward due to the servo motor 58 coacting with camming surface 59, and the mandrel will retract to its original position while ejection means, e.g. eject wheels, in the ejection section 32, will engage the enhanced tube and send it into the cavity measurement section 18. Once the enhanced tube is completely in the cavity measurement section 18 and the front mandrel is in its original position the rear mandrel 24 will now drop down and the process will repeat itself.

Figure 4:
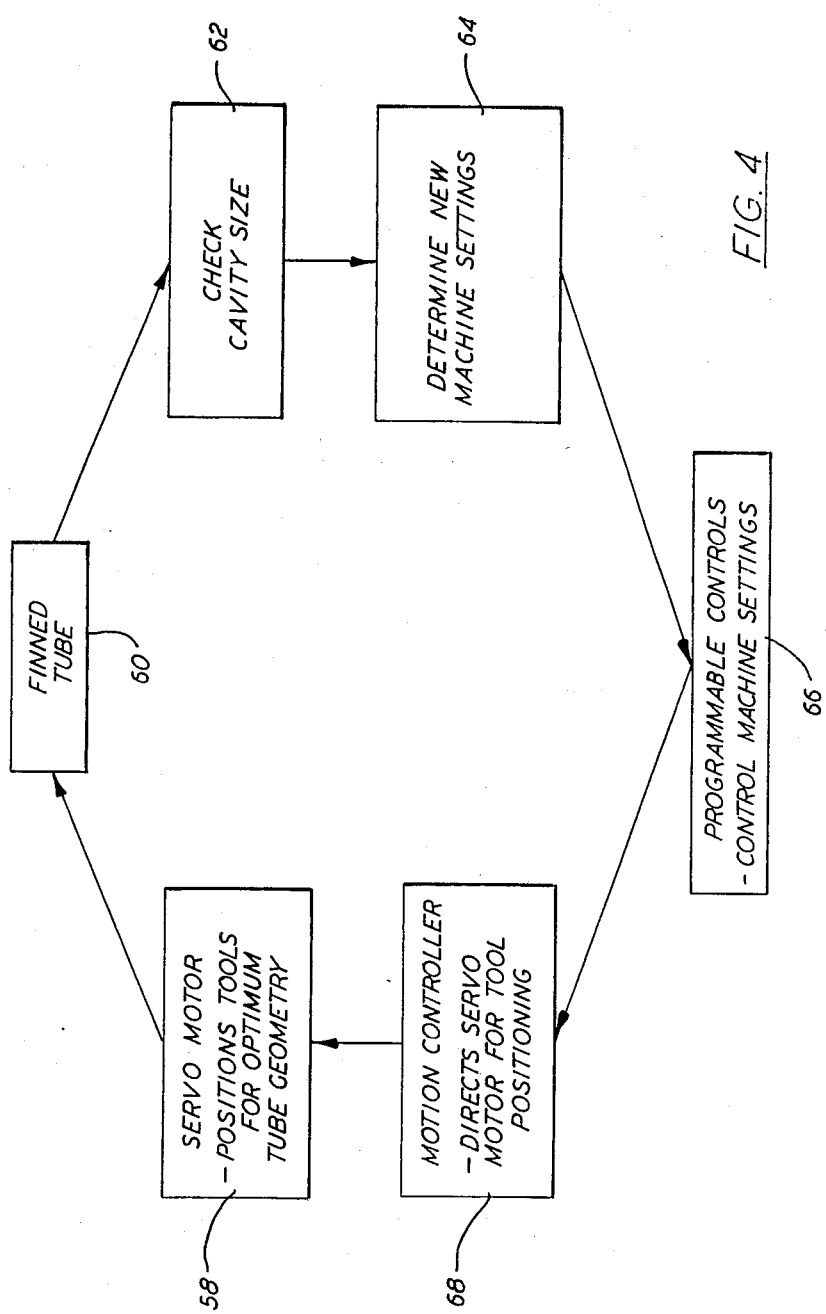
FIG. 4 is a block diagram of a tube finning machine as shown in FIG. 1.

A closed loop process for the manufacture of enhanced tubes and for measuring the pore size of the enhanced tube in accordance with this invention is shown schematically in block form in FIG. 4. The process includes enhancing means 60 for finning the tube, checking means 62 for measuring the pore size of the enhanced tube, processing means 64 for performing calculations of the data from the checking means and determining new machine settings, control means 66 for controlling the machine settings, motion controlling means 68 for interfacing between the programmable controller that sequences numerous functions and the servo motor that actually moves the tool arbors, and positioning means or servo motor 58 for positioning the tool arbors for optimum tube geometry.

Figure 6:
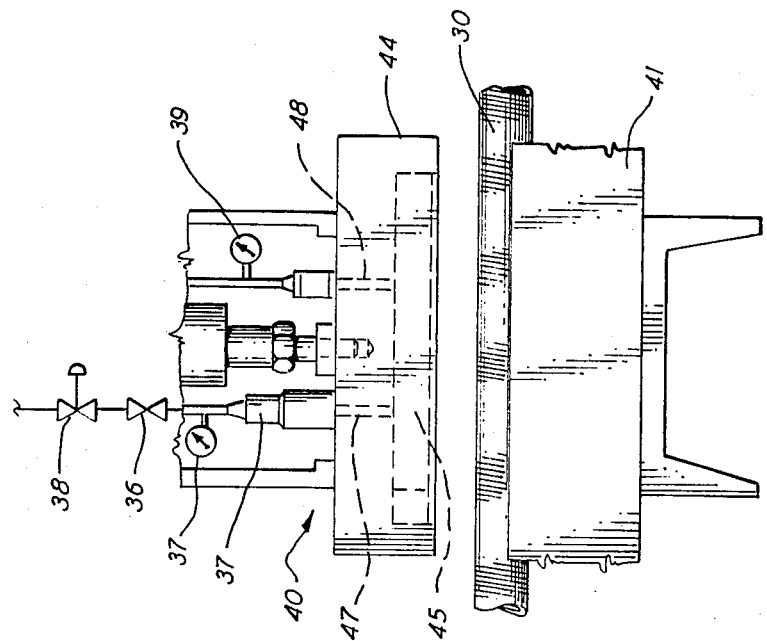
FIG. 6 is a front elevation view of the pore measuring device shown in FIG. 5.
Figure 5:
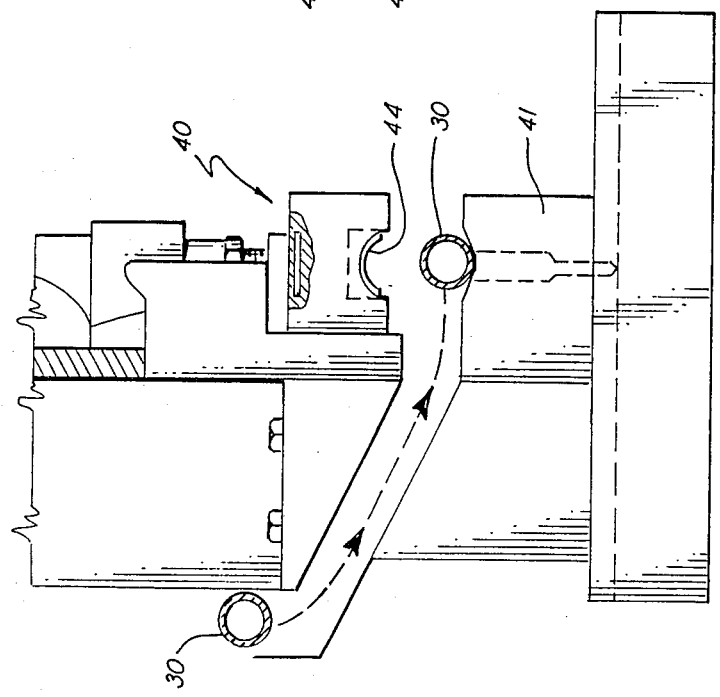
FIG. 5 is a side elevation view of a pore measuring device of the present invention.

Referring now to FIGS. 5 and 6 there is illustrated an enhanced tube 30, which after it is completely in the cavity measurement section drops down along the path as shown by the arrows and enters channel support 41. The tube is thus supported in a channel support 41 below the pore measurement tool 40. With the enhanced tube in the channel support 41, the measuring tool 40 is lowered so that the flexible insert 44 matingly engages with the surface of the tube 30. In operation, the air inlet 47 is supplied with constant pressure air by air regulator 38. The constant pressure air from the air regulator 38 then flows through flow control valve 36. The pressure downstream of flow control valve 36 is read at gage 37. Further, a portion of the air pressure flowing through chamber 45 is lost across the subsurface channels and pores of the tube. The remaining air pressure is measured by pressure gage or manometer 39 at outlet 48. Thus, the difference between the pressure on pressure gage 37 and gage 39 gives the pressure drop across the pores, which is a measure of the average pore size on the tube. This average pore size measurement can be determined by measuring the boiling heat transfer coefficient of tubes having a known pressure drop across their pores and determining the optimum pore size. A correlation can thus be established between the pressure drop across the pores and the expected boiling heat transfer coefficient.

The theory involved in this invention is that the pressure drop across an orifice is a function of the area of the orifice. Accordingly, in the present method of measuring the pore size of an enhanced tube, compressed air is blown through the pores, and the resulting pressure drop gives a measure of the average size of the pores on the enhanced tube. The pressure drop across the pores of the tubes correlate to the expected boiling heat transfer coefficient of the tube. The supply air pressure varies depending on the setting of the air regulator 37. The pressure at gage 37 is thus controlled by flow control valve 36. Typically, the flow control valve is set so that one-half of the pressure is dropped across it and gage 37 will read 2.0 psig. A typical supply pressure is 4.0 psig. Thus, when the enhanced tube to be tested has the exact right pore size, i.e. a known pressure, 1.0 psig, is lost across the tube, the pressure at the pressure gage 39 will be a precise known value, e.g. 1.0 psig. A slight decrease in the pore size will cause the pressure gage to see a slight increase in pressure, while a slight increase in the pore size will cause the pressure gage to see a slight decrease in pressure from the precise desired value.

Of course, the foregoing description of a method for measuring the pore size in an enhanced tube is directed to a preferred embodiment, and various modifications and other embodiments of the present invention will be readily apparent to one of ordinary skill in the art to which the present invention pertains. Therefore, while the present invention has been described in conjunction with a particular embodiment it is to be understood that various modifications and other embodiments of the present invention may be made without departing from the scope of the invention as described herein and as claimed in the appended claims.

What is claimed is:

1. A method of determining the average size of a plurality of pores on the external surface of an enhanced tube, comprising the steps of:
    positioning a pressure measurement apparatus on a portion of the external surface of the enhanced tube, the enhanced tube having a plurality of subsurface channels connected by a plurality of the pores along the channels, said pressure measurement apparatus having an single inlet connected to a single source of fluid of known pressure and an outlet;
    supplying said fluid of known pressure to said single inlet whereby said fluid flows into said pressure measurement apparatus and through the pores and subsurface channels beyond the portion of the external surface covered by said pressure measurement apparatus;
    sensing the pressure of the fluid in said pressure measurement apparatus;
    determining the difference between the sensed pressure in said pressure measurement apparatus to said known pressure source; and
    comparing the determined difference to a selected pressure, wherein said selected pressure correlates to the desired average size of the pores on the external surface of the enhanced tube.

2. A method of determining the average size of a plurality of pores on the external surface of an enhanced tube as set forth in claim 1 including providing said pressure measurement apparatus with a flexible insert to matingly engage the perimeter of said portion of the external surface where a portion of the known fluid pressure supplied to said pressure measurement is lost across the surface of the enhanced tube.

3. A method of determining the average size of a plurality of pores on the external surface of an enhanced tube as set forth in claim 1 wherein said selected pressure is equivalent to an enhanced tube having an optimum boiling heat transfer coefficient.

4. A method for determining the average size of a plurality of pores on the external surface of an enhanced tube having a plurality of helically extending subsurface channels connected by a plurality of pores along the channels comprising the steps of:
    positioning a pressure measurement apparatus having a single inlet and a single outlet on a portion of the external surface of the enhanced tube so as to define therewith a chamber with the apparatus and the enhanced tube defining an area of circumferential contact with the pores on the external surface forming leakage paths at the area of circumferential contact;
    supplying fluid at a known pressure to the inlet whereby the fluid flows into the chamber with a first portion flowing from the chamber via the outlet and a second portion flowing from the chamber via the pores forming leakage paths;
    sensing the pressure at the outlet;
    comparing the pressure at the inlet and outlet to determine the difference which is an indication of the average pore size.

* * * * *